(12) United States Patent
Kivistö

(10) Patent No.: US 8,977,351 B2
(45) Date of Patent: Mar. 10, 2015

(54) DISPOSABLE HEART RATE INDICATOR

(75) Inventor: Kari Kivistö, Oulunsalo (FI)

(73) Assignee: Spektikor Oy, Oulu (FI)

( * ) Notice: Subject to any disclaimer, the term of this patent is extended or adjusted under 35 U.S.C. 154(b) by 147 days.

(21) Appl. No.: 13/303,744

(22) Filed: Nov. 23, 2011

(65) Prior Publication Data

US 2012/0136265 A1    May 31, 2012

(30) Foreign Application Priority Data

Nov. 26, 2010    (FI) ..................... 20106249

(51) Int. Cl.
| | | |
|---|---|---|
| *A61B 5/04* | (2006.01) | |
| *A61B 5/00* | (2006.01) | |
| *A61B 5/02* | (2006.01) | |
| *A61B 5/024* | (2006.01) | |
| *A61B 5/0245* | (2006.01) | |

(52) U.S. Cl.
CPC ......... *A61B 5/02438* (2013.01); *A61B 5/02455* (2013.01); *A61B 2560/0412* (2013.01); *A61B 2562/164* (2013.01)
USPC ............................ 600/519; 600/301; 600/485

(58) Field of Classification Search
CPC .................. A61B 5/0402; A61B 5/006; A61B 2560/0412; A61B 5/6822; A61B 5/6832; A61B 2560/0468; A61B 5/6823; A61B 5/6833; A61B 5/02438
USPC ......... 600/508–510, 513, 515, 519, 523, 528, 600/549, 300, 485, 301
See application file for complete search history.

(56) References Cited

U.S. PATENT DOCUMENTS

| | | | |
|---|---|---|---|
| 4,700,708 A | 10/1987 | New, Jr. et al. | |
| 8,434,421 B2 * | 5/2013 | Fagan | 116/309 |
| 8,594,776 B2 * | 11/2013 | McCombie et al. | 600/513 |
| 2005/0277841 A1 * | 12/2005 | Shennib | 600/511 |
| 2006/0030781 A1 | 2/2006 | Shennib | |
| 2006/0030782 A1 * | 2/2006 | Shennib | 600/509 |

(Continued)

FOREIGN PATENT DOCUMENTS

| | | |
|---|---|---|
| EP | 1 609 415 A1 | 12/2005 |
| WO | WO 03/024325 A2 | 3/2003 |
| WO | WO 2008/020376 A2 | 2/2008 |

OTHER PUBLICATIONS

Finnish Search Report issued in Finnish Application No. 20106249 on Jul. 15, 2011 (with translation).

(Continued)

*Primary Examiner* — Catherine Voorhees
(74) *Attorney, Agent, or Firm* — Oliff PLC (57) ABSTRACT

A disposable heart rate indicator is provided. The disposable heart rate indicator has a power source for generating power to the heart rate indicator, at least two electrodes for detecting a person's heart beat, a processor and a light signal emitting head. The processor is operatively coupled to the at least two electrodes and is configured to receive a signal on each heart beat detected by the electrodes and visually indicate a detected heart rate via optical light emitted by the light signal emitting head. The heart rate indicator further includes a conductor coupled between the light signal emitting head and the processor. The conductor is arranged to extend from a heart beat detection area formed by the electrodes and the processor such that the light signal emitting head is visible during use.

19 Claims, 3 Drawing Sheets

(56) References Cited

U.S. PATENT DOCUMENTS

| | | | |
|---|---|---|---|
| 2007/0249946 A1 | 10/2007 | Kumar et al. | |
| 2008/0058614 A1* | 3/2008 | Banet et al. | 600/300 |
| 2008/0091090 A1* | 4/2008 | Guillory et al. | 600/301 |
| 2008/0146895 A1* | 6/2008 | Olson et al. | 600/301 |
| 2008/0275327 A1 | 11/2008 | Faarbaek et al. | |
| 2008/0312522 A1* | 12/2008 | Rowlandson et al. | 600/382 |
| 2008/0319278 A1* | 12/2008 | Omtveit et al. | 600/301 |
| 2009/0318779 A1* | 12/2009 | Tran | 600/301 |
| 2010/0286607 A1 | 11/2010 | Saltzstein | |
| 2012/0232398 A1* | 9/2012 | Roham et al. | 600/453 |

OTHER PUBLICATIONS

European Search Report dated Mar. 16, 2012 issued in European Patent Application No. 11190444.7.

* cited by examiner

DISPOSABLE HEART RATE INDICATOR

FIELD

The invention relates to indicating a heart rate, and particularly to indicating a heart rate by a disposable heart rate indicator.

BACKGROUND

There are situations wherein several persons are seriously wounded or injured simultaneously. This may happen in war zones or owing to a road accident, for instance. In such cases, it is important to be able to establish easily and reliably who among the injured or wounded is or are most in need of help, in other words closest to losing their lives, so as to enable such a person or persons to be helped first.

When a person's vital functions are threatened with coming to an end e.g. because of a bleeding wound, the heart tries to pump blood to the circulation at a high pace. In such a case, the heart beat frequency, i.e. heart rate or pulse, increases rapidly. A known manner to find these wounded or injured persons most in need of help is thus to try their pulse by using a finger on the jugular area, for instance. This, however, takes a lot of time, since in practice there may be several people to be monitored simultaneously. In addition, the aforementioned manner is unreliable since no pulse is necessarily found by the finger technique at once, a person's own pulse may influence the indication of another person's pulse, and the person taking the pulse should be capable of distinguishing differences in the heart rates of several different people. Furthermore, the aforementioned manner subjects a patient's jugular area to air, which may be cold.

It is also known to detect a pulse by using a stethoscope, but background noise is very often so overwhelming that in practice pulse detection by hearing is not reliable.

It is also known to measure a heart rate by means of heart rate monitors for athletes. These, however, are expensive, and it is time-consuming to place such a device on a wounded person.

A disposable heart beat detection device is known from WO 03024325. The heart beat is indicated by means of light or sound signals. This solution has at least the problem that a wounded person is to be undressed in the area of the heart beat detection device (e.g. in the thorax area) so as to enable the heart beat to be detected visually by means of light signals emitted by the heart beat detection device. Further, the wounded person has to lie down with his or her back towards the ground in order for the heart beat detection area to be facing upwards and thus in order for the light signal to be visible.

It is thus important to find a faster, more reliable, and more user-friendly method of indicating a heart rate.

BRIEF DESCRIPTION

An object of the invention is to provide a disposable, improved heart rate indicator.

The objects of the invention are implemented by a device which is characterized by what is stated in the independent claims.

BRIEF DESCRIPTION OF FIGURES

The invention is now described in closer detail in connection with preferred embodiments and with reference to the attached drawings, in which.

DESCRIPTION OF EMBODIMENTS

Figure 1:
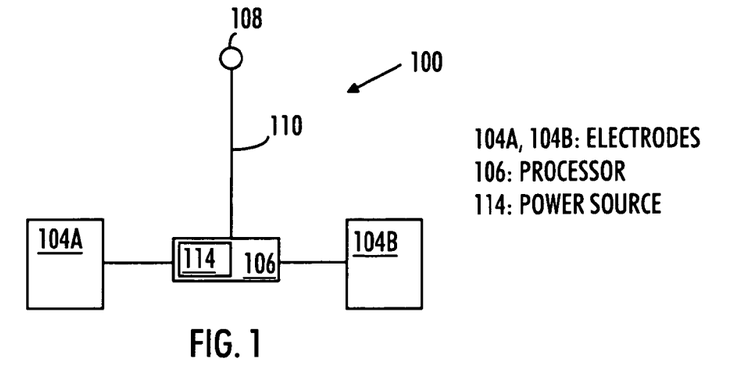
FIG. 1 shows a heart rate indicator according to an embodiment.

FIG. 1 shows a disposable, portable heart rate indicator according to an embodiment. In this context, a heart rate refers to how many times a person's heart beats per minute. In other words, a person's heart rate equals the person's pulse. The disposability of the heart rate indicator 100 arises from the fact that the heart rate indicator 100 is economically extremely inexpensive to manufacture. Thus, it may be disposed of after having been used for indicating one person's heart rate. On the other hand, when the heart rate indicator 100 is used in a war zone, accident area or in similar conditions, it may be very important to keep good hygiene among different persons. In such a case, it is not recommendable to use the same heart rate indicator 100 on two different persons. This sets clear conditions for the manufacture of the heart rate indicator 100. This partly explains why athletic heart rate monitors are excluded from this particular use since, typically, the athletic heart rate monitors for sports use are very expensive and thus too valuable to be used only once.

The disposable heart rate indicator 100 is designed for indicating a heart rate of a substantially immobile person. This is sufficient since, typically, persons whose heart rate is being detected are seriously injured. If a person can move after being injured, it is likely that this person is not the first person in need of help.

The disposable heart rate indicator 100 may further comprise at least two electrodes 104A, 104B for detecting a person's heart beat, the electrodes 104A, 104B being attachable to the person's skin during use. The number of electrodes may be more than two, but in order to provide a reliable heart rate indication at least two electrodes 104A, 104B are required. This enables an electrocardiogram to be measured. In order to detect a heart beat, it is sufficient to detect peaks points, i.e. R peaks, of the electrocardiogram therefrom.

Since the size of the necessary electrodes is smaller than in that of the electrodes for sports use, the electrodes 104A, 104B are inexpensive to manufacture and they may be packed in a small space, which thus makes them suitable for the disposable heart rate indicator 100. In an embodiment, the size of the electrically exposed part of the electrodes is no more than 20 mm in diameter. In another embodiment, the dimensions of the active part of the electrodes are no more than 20 mm×20 mm.

The disposable heart rate indicator 100 may further comprise a processor 106 and a light signal emitting head 108, the processor 106 being operatively coupled to at least two electrodes 104A, 104B. The coupling may be carried out by means of electrical conductors, for instance. The processor 106 is configured to receive a signal on each heart beat detected by the electrodes 104A, 104B. In other words, when the electrodes 104A, 104B detect an R peak in the electrocardiogram, the electrodes 104A, 104B emit an electric signal to the processor 106. In addition, the processor 106 may filter off frequencies outside the heart rate frequency band (typically 1 to 4 Hz) and amplify a received signal of the order of millivolts e.g. to a thousand-fold signal. This results in a voltage of the order of volts.

The processor 106 may visually indicate a detected heart rate by means of optical light emitted by the light signal emitting head 108. For instance, the processor 106 may cause the light signal emitting head 108 to flash in accordance with the pace of the detected heart beats. In other words, when the electrodes 104A, 104B detect a heart beat and emit a signal to the processor 106, the processor 106 may temporarily turn the emission of light on or off. Such turning on/off may take place e.g. such that the processor 106 cuts the power supplied to a light source which produces light to be emitted from the light signal emitting head 108. For the sake of simplicity, the figures show no light source.

In an embodiment, the light signal emitting head 108 comprises a digital display enabling a person's detected heart rate to be indicated numerically either together with a flashing light or instead thereof. In this case, the light signal emitting head 108 may emit optical light which, e.g. by means of a liquid crystal display (LCD) connected to the light signal emitting head 108, is made to indicate a numerical reading. The power necessary for the liquid crystal display and the processor may also in this case be placed in connection with the light signal emitting head 108, or power and control may be brought from a power source 114 and the processor 106 via conductor means.

According to an embodiment, the disposable heart rate indicator 100 further comprises conductor means 110 coupled between the light signal emitting head 108 and the processor 106, the conductor means 110 being configured to extend from a detection area formed by the electrodes 104A, 104B and the processor 106. This solution enables the light signal emitting head 108 to be visible during use. In other words, the light signal emitting head 108 is located separately from the detection area. When the detection area is covered by pieces of clothing, for instance, the conductor means 110 are configured to bring the light signal emitting head 108 outside the clothing, thus making it visible.

In an embodiment, the light signal emitting head 108 may be brought visible e.g. from between the skin and the pieces of clothing via a neckline to the face area. In another embodiment, the light signal emitting head 108 may be brought visible e.g. from beneath a sleeve of a piece of clothing to the hand area. In an embodiment, the light signal emitting head 108 may be brought visible e.g. from between buttons of pieces of clothing onto the clothing. The detection area will be described in closer detail in connection with FIG. 5.

Figure 2A:
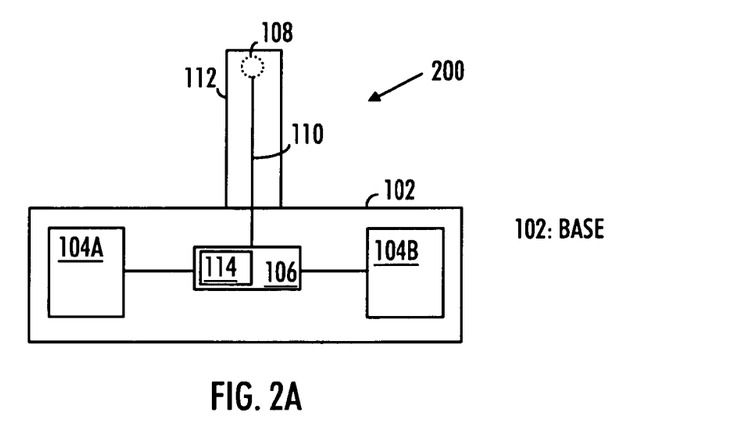
FIGS. 2A and 2B show a heart rate indicator according to an embodiment.

FIG. 2A shows a disposable heart rate indicator 200 according to an embodiment, as seen from a side of the heart rate indicator to be placed against a person's skin for detecting the person's heart rate. According to an embodiment, the disposable heart rate indicator 200 comprises a base 102. The base 102 may be made from fabric or leather, for instance.

According to FIG. 2A, at least two electrodes 104A, 104B and a processor 106 are fixedly installed in the base 102. The installation may be implemented by embedding the electrodes 104A, 104B and the processor 106 in the base, or by attaching the electrodes 104A, 104B and the processor 106 to a surface of the base 102 e.g. by gluing.

The disposable heart rate indicator 200 and the conductor means 110 are coupled between the light signal emitting head 108 and the processor 106, the conductor means 110 being configured to extend from the base 102. This enables the light signal emitting head 108 to be visible during use. The conductor means 110 may comprise e.g. an optical or electrical conductor. In the case of an optical conductor, the optical conductor may be e.g. an optical fibre, whereby a light-producing light source may be located in connection with the processor 106 in the base 102, and the light signal emitting head 108 is an optically transparent aperture allowing light to pass out of the optical conductor, such as an optical fibre. In the case of an electrical conductor, the light-producing light source may be located in connection with the light signal emitting head 108 in the base 102 and thus outside the detection area as well. The processor 106 may then supply power to the light source residing outside the base 102. The light-producing light source may be a light emitting diode, for instance. In such a case, the light signal emitting head 108 may be an optically transparent aperture, such as an opening or glass, around or in front of the light emitting diode. In an embodiment, the light signal emitting head 108 is only a light emitting diode (LED).

Figure 2B:
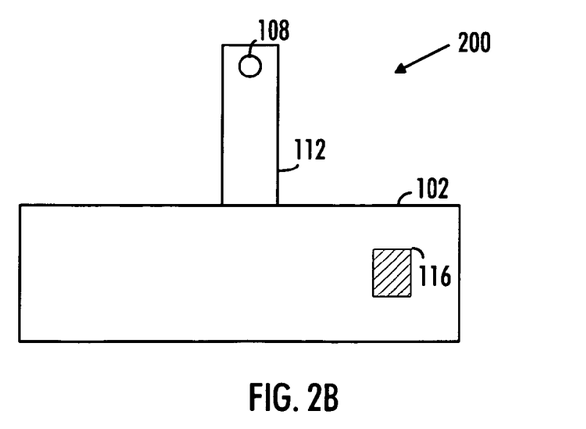

The disposable heart rate indicator 100/200 may further comprise a power source 114 for generating power to the heart rate indicator 100. In the case of FIGS. 2A and 2B, the power source 114 is fixedly installed in the base. The installation may be implemented in a manner similar to that used for attaching the processor 106 and the electrodes 104A, 104B to the base 102. The power source 114 generates power to the electrodes 104A, 104B and the processor 106 as well as to the light source (not shown in the figures) which, as discussed above, may be located in the base 102 or outside the base 102 and the detection area. During storage of the heart rate indicator 100, the power source 114 may be in a passive mode, consuming no energy stored therein. When the heart rate indicator 100 is put to use, the power source is activated e.g. by removing an insulating or protective layer from above the poles of the power source 114. The activation may also be implemented by subjecting the power source 114 to air or to a temperature difference between the person's skin and the surrounding air. Such activation is possible when the power source 114 to be used is e.g. a zinc-air accumulator. The power source 114 may be designed such that it produces power to the heart rate indicator 100 at least for three hours from the activation of the power source 114. In an embodiment, the activation of the power source 114 takes place by removing an insulating layer from above the poles of the power source 114 and placing the electrodes 104A, 104B against a person's skin. In such a case, when the electrodes 104A, 104B detect an electric contact on the person's skin, the power source 114 becomes activated. An advantage of this embodiment is that if, for some reason or another, the insulating layer becomes detached from above the poles, the power source does not, however, start consuming power before the heart rate indicator is really put to use.

The power source, as the entire heart rate indicator 100/200, may be manufactured such that after use it may be disposed of as mixed or general waste. This has been achieved e.g. such that energy-storing cells of the power source 114 are made from a biodegradable material or do not contain any detrimental substances which might prevent the cells from being disposed of as mixed or general waste.

According to an embodiment, the processor 106 is by means of the light signal emitting head 108 configured to indicate at least one of the following: the electrodes 104A, 104B detect no heart beat, the power source 114 is running low, and the heart rate indicator 100/200 is ready for operation in connection with being put to use. The indication may take place by means of a light signal emitted from the light signal emitting head 108. This light signal may be e.g. a continuous light signal or a light signal having a color different from that of a light signal indicating the heart rate. For instance, when the heart rate indicator 100 is put to use by activating the power source 114, the processor 106 may via the light signal emitting head 108 indicate readiness for operation such that the light signal emitting head 108 emits a continuous optical light. When the heart rate indicator 100 detects a heart beat, the continuously lit optical light goes out and a light at the light signal emitting head 108 starts flashing in accordance with the detected heart rate. This has the advantage that the medical staff immediately knows whether or not the heart rate indicator 100/200 is ready for operation or, for instance, whether something has happened during storage that has made the heart rate indicator 100 inoperative. If no light is lit upon activation of the power source 114, the heart rate indicator 100 may be broken.

If the electrodes 104A, 104B detect no heart beat at all, the processor 106 may turn the light emitted from the light signal emitting head 108 on or off. In such a case, the medical staff immediately sees if the heart rate indicator 100 detects no heart rate. The reason why no heart beat is detected may be because of the electrodes 104A, 104B (poor contact between the skin and at least one electrode 104A, 104B, for instance) or it may be because the person whose heart rate is to be detected is dead.

Figure 7A:
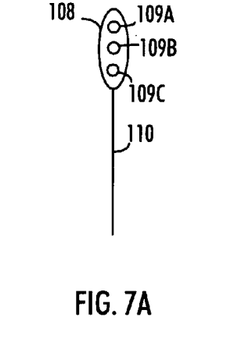
FIGS. 7A and 7B show a light signal emitting head according to some embodiments.

If the power source 114 is running out, the processor 106 may cause an optical light having a certain color to be lit either temporarily or continuously. In such a case, the medical staff immediately sees if the power is running out on a heart rate indicator 100 being used. This enables the particular heart rate indicator 100 to be replaced immediately. A different color may be provided such that several light sources are in use that produce visible, i.e. optical, light having different wavelengths. Alternatively, a light source may use the same wavelength but the light signal emitting head 108 may comprise a plurality of apertures 109A to 109C which may be covered by differently-colored pieces of glass or corresponding optically transparent materials, as shown in FIG. 7A. The processor 106 may control which aperture is to be used at a given time in order to produce light of a certain color.

As a patient's trauma progresses, e.g. as a consequence of internal bleeding, the patient's heart rate is the first fact to indicate a change for the worse. An increasing heart rate indicates an immediate need for medical treatment. Therefore, in an embodiment, the processor 106 is configured to divide a heart rate area into at least two sub-areas. In the case of three sub-areas, the sub-areas may be e.g. the following: less than 50 beats per minute, 51 to 105 beats per minute, and more than 105 beats per minute. The processor 106 may thus, by means of the light signal emitting head 108, emit optical light of a predetermined color, wherein the color of the emitted optical light is determined according to the sub-area in which the person's heart rate is at the particular moment. In other words, the heart rate indicator 100/200 may indicate a change in the heart rate of the patient by means of differently-colored lights and/or by accelerating flashing of light. The different colors may be produced as mentioned above and shown in FIG. 7A. The processor 106 may be configured, by means of the light source and the light signal emitting head 108, to produce e.g. blue flashing light when the heart rate resides within the sub-area of 51 to 105 beats per minute, and red, more frequently flashing light when a person's heart rate is more than 105 beats per minute. This is advantageous in that the medical staff very quickly at a glance is able to see which patient needs immediate treatment.

The disposable heart rate indicator 200 may further comprise protective means 112 for protecting the conductor means 110, such as an optical or electrical conductor, from external factors. However, such protective means are not compulsory, as can be seen in FIG. 1. The conductor means 110 may be integrated into the protective means 112. In such a case, the protective means 112 are the first to receive potentially harmful impacts and other blows caused by external factors.

In an embodiment, the protective means 112 may be made from a flexible and supple material, such as fabric or leather, to enable the protective means 112 to be easily placed against a person's skin.

In another embodiment, the protective means 112 may be made from a solidifiable, plasticizable or mouldable material which allows the light signal emitting head 108 to be placed into a certain position by means of the protective means 112.

FIG. 2B shows the disposable heart rate indicator 200 according to the embodiment of FIG. 2A as seen from a side of the heart rate indicator 100 which is not to be placed against a person's skin during use. The light signal emitting head 108 is now shown in uniform linear markings since the light signal emitting head 108 is used on this side of the heart rate indicator 200. In other words, the light signal emitting head 108 emits light in this direction.

FIG. 2B further shows a fastening element 116 which may be an adhesive surface or a detachably attaching glue surface, for instance. A use of this fastening element 116 is described in connection with FIGS. 3A to 3C.

Figures 3A, 3B, 3C:
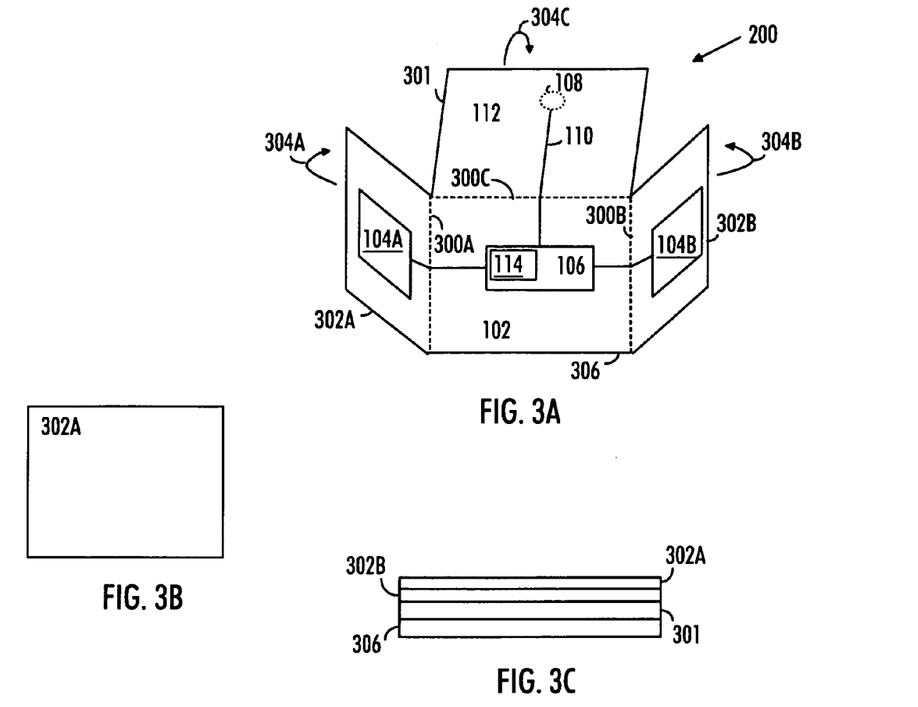
FIGS. 3A, 3B, and 3C show how a heart rate indicator may be folded up for storage according to an embodiment.

FIGS. 3A, 3B, and 3C show how the disposable heart rate indicator 100 may be folded up for storage. FIG. 3A shows that the heart rate indicator 100 may be folded up e.g. at three points 300A to 300C shown in broken line. In an embodiment, the heart rate indicator 100 may be folded up for storage such that sections of the heart rate indicator 100 which in use are placed against a person's skin constitute no part of an outer surface of the folded heart rate indicator 100. This may be achieved e.g. as follows. First, the protective means 112 and a section 301 comprising part of the conductor means 110 are folded at the point 300C onto a section 306 of the base 102 as shown by arrow 304C. Although in FIG. 3A the section 306 comprises a processor 106 and a power source 114, this is not necessary, but the folds may also be made differently or at different points. This particular folding enables the conductor means 110 to be wrapped inside the folded heart rate indicator 100 for the duration of storage. Next, a section 302B of the base 102 is folded at the point 300B as shown by arrow 304B onto the section 306 and the section 301 folded thereon. The section 302B may further comprise a glue or adhesive surface 116, as shown in FIG. 2B. Finally, a section 302A may at the folding point 300A be folded as shown by arrow 304A onto the rest of the sections 306, 301, and 302B. The adhesive or glue surface 116 shown in FIG. 2B may then become attached to a surface facing the electrode 104A of the section 302A of the base 102, thus holding the folded heart rate indicator 200 together during storage. FIG. 3B is a top view showing the folded disposable heart rate indicator 200. The topmost part is the non-electrode side of the section 302A. FIG. 3C is a side view showing the folded heart rate indicator 200, with different layers clearly visible. The lowest layer is the middle section 306 of the base 102, then comes the section 301, next the section 302B of the base 102 and, on top, the section 302A of the base 102. Of course, the folding order of the sections 302A and 302B may be changed, depending on the section in which the fastening means 116 of FIG. 2B reside.

The dimensions of the base 102 of the disposable heart rate indicator 200 may be e.g. 150 mm×40 mm (length×width)

when unfolded, and 50 mm×40 mm when folded up. As seen in FIG. 3A, the width of the protective means 112 (i.e. the section 301) may be similar to that of the section 306, i.e. as wide as the section of the base 102 onto which the rest of the sections are to be folded. In an embodiment, the dimensions of the protective means are 50 mm×280 mm. In such a case, the 280 mm long section may be folded many times onto the section 306 of the base. The fact that the sections 306 and 301 are of the same width is advantageous in that it enables the power source 114 located in the section 306 to be protected in a reliable manner. In addition, the folded heart rate indicator 200 (FIGS. 3B and 3C) then becomes uniform in thickness, which makes it durable.

Folding provides several advantages. First, storage requires less space. Second, since the sections of the heart rate indicator 200 that in use are placed against a person's skin constitute no part of the outer surface of the folded heart rate indicator 200, these sections remain sterile and/or clean for subsequent use. As can be seen in FIGS. 3B and 3C, the outer surface of the folded heart rate indicator 200 consists of the surfaces of the section 306 and the section 302A that are not placed against a person's skin during use. Furthermore, the power source 114 thus becomes protected. If, for example, the power source is activated when its poles become detached from the insulating surface (section 301 in FIG. 3A) or the power source is activated when the accumulator becomes subjected to air or a given temperature difference, it is possible to keep the power source in the folded heart rate indicator 200 passive during storage and become activated when the folded heart rate indicator 200 is unfolded (i.e. when the section 301 is lifted from top of the power source). In fact, in an embodiment the protective means 112 serve as an insulating part for the power source 114.

In an embodiment, the conductor means 110 are arranged inside the heart rate indicator that has been folded up for the duration of storage, and in use arranged to extend from the base 102 such that the light signal emitting head 108 is visible during use. As can be seen in FIGS. 3A and 3C, the conductor means 110, being part of the section 301, are enveloped by the folded heart rate indicator 200 when the heart rate indicator 200 is folded up for storage. When the folded heart rate indicator 200 is unfolded for use, the section 301 is turned away from above the base 102, thus making the conductor means 110 to extend from the base 102 during use.

Figure 4:
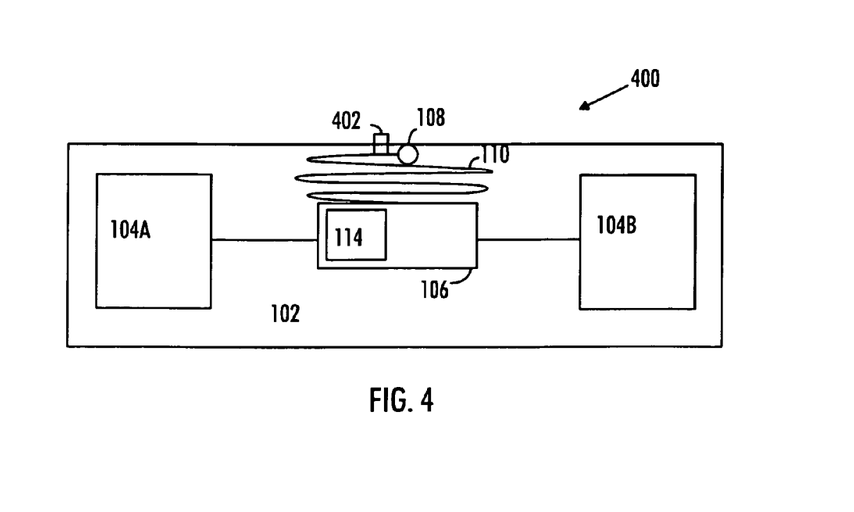
FIG. 4 shows a heart rate indicator according to an embodiment.

The conductor means 110 of a heart rate indicator 400 shown in FIG. 4 comprise e.g. an optical or a current conductor whose end is provided with a light signal emitting head 108. Such conductor means 110, which have no protective means according to FIGS. 2 and 3, may e.g. by gluing be fastened to the base 102 for the duration of storage. The current or optical conductor may be fastened in a wire-like manner to the surface of the base 102. In such a case, when the base 102 is being folded up for storage, folds are only provided at the points 300A and 300B of FIG. 3A, and the folded heart rate indicator of FIG. 3C has no layer 301 (the layer 301 in practice being the conductor means 110 glued/taped to the surface of the base 102). This conductor means solution is advantageous in that the conductor means 110 may be very long.

Figure 6:
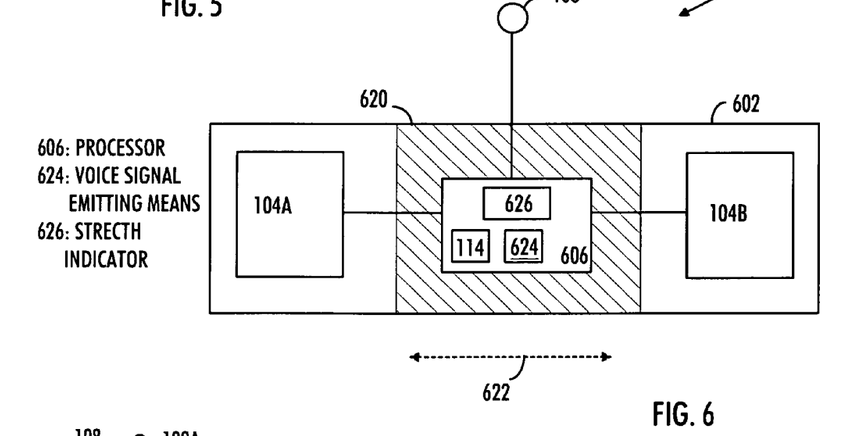
FIG. 6 shows a heart rate indicator according to an embodiment.

In an embodiment, the conductor means 110 comprise a detachment part 402 which may be e.g. a plastic part located off the surface of the base 102. The detachment part 402 may be used when the conductor means 110 are being detached from the base 102 when the heart rate indicator 400 is put to use. This is because the detachment part 402 located off the base 102 (not glued thereto) is easy and quick to grab and, by pulling at the detachment part 402, the conductor means 110 may be pulled out of the base 102 to extend therefrom. When the heart rate indicator 400 according to FIG. 4 is put to use, the conductor means 110 are pulled out so as to extend them lengthwise, as seen in FIGS. 1 and 6.

Figure 5:
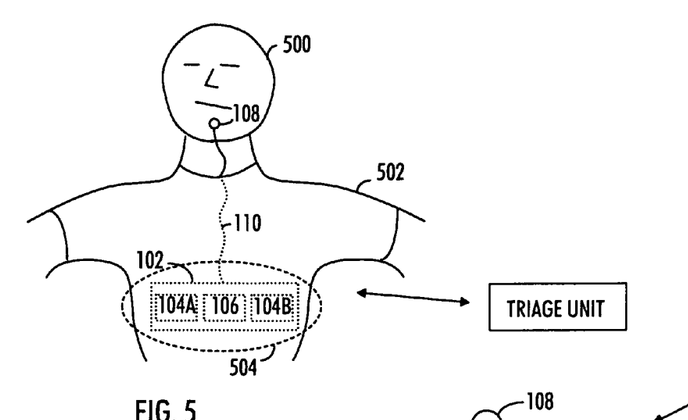
FIG. 5 shows how a heart rate indicator is placed on a person for indicating the person's heart rate according to an embodiment.

FIG. 5 shows how the disposable heart rate indicator may be used for indicating a person's 500 heart rate. According to an embodiment, the heart rate indicator is placeable on the person's 500 chest. The heart rate indicator may be placed e.g. under the person's 500 clothes 502. In such a case, if a light signal emitting element were attached to the base 102, no light signal would be visible. It is also not recommendable to tear or take off the clothes since then the person 500 could be subjected to cold or rain. According to the embodiment, the light signal emitting head 108 may, by means of the conductor means 110, be exposable from underneath the person's 500 clothes 502 so as to make it visible. This is advantageous in that the light signals emitted by the light signal emitting head 108 are visible without the base 102 itself being visible. In other words, the conductor means 110 enable the light signal emitting head 108 to be brought visible during use even if the visibility of the base 102 would be prevented during use e.g. owing to pieces of clothing, i.e. the base 102 would be located underneath the clothes such that it would be impossible to see the base 102. The base 102 and the conductor means 110 should be made such that they can be placed under clothes. In FIG. 5, sections shown in dotted line are located underneath the clothes 502.

FIG. 5 also shows a heart beat detection area 504 formed by an area formed by the electrodes 104A, 104B and the processor 106. In practice, this area comprises the area of a person's chest in which the disposable heart rate indicator could be placed in order to enable the person's heart rate to be detected by the heart rate indicator.

Figure 7B:
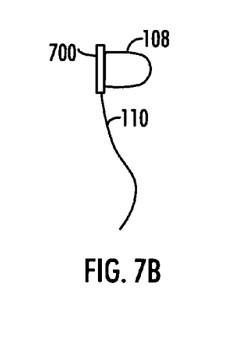

In an embodiment, as shown in FIG. 7B, the heart rate indicator comprises fastening means 700 for fastening the light signal emitting head 108 to a person. The fastening means 700 may comprise e.g. a glue surface, sticky tape, fastening clip or corresponding means enabling the light signal emitting head 108, e.g. a light emitting diode, to be fastened to a person's skin or clothes. These fastening means 700 may be connected to the light signal emitting head 108. In an embodiment, the light signal emitting head 108 comprises as the fastening means 700 one surface which is attachable e.g. by glue or tape to the person's 500 skin or clothes. This is advantageous in that the light signal emitting head 108 remains visible all the time. In other words, the light signal emitting head 108 does not move. In such a case, it is possible to make the direction in which the light signal emitting head 108 emits light to remain the same all the time.

A common problem with detecting an electrocardiogram is movement between the electrodes and the skin. This is a problem in athletic use in particular. The heart rate indicator 100 according to the embodiment is meant for indicating a heart rate of an immobile person. However, in many cases in order to be able to detect a weak heart rate, in an embodiment the electrodes are provided with a glue or adhesive surface so as to during use reliably remain attached to a person whose heart beats are to be detected. In addition, the electrodes may be provided with a gel surface in order to improve conductivity between a person's skin and the electrodes. During storage, the glue surface may be provided with a protective coating, such as a piece of plastic, tape or the like to keep the glue surfaces intact during storage. Providing the electrodes with glue surfaces contributes to the disposability of the heart rate indicator. When the tape is removed from the glue surface, the electrode is placed on (glued to) a person's skin and, after use, removed from the skin, so the electrode can subsequently no longer be used as reliably for another person. This may be because the glue surface of the electrode is no longer as strong as it was with the first person, or because the gel surface has worn off in connection with the first person.

In another embodiment, the base is at least partly made from a flexible material, the power source 114, the at least two electrodes 104A, 104B, and the processor 606 being fixedly installed therein. The electrodes 104A, 104B are installed in the base such that a distance between the electrodes 104A, 104B may change owing to the flexibility of the base. In an embodiment, a middle part of the base is made of a rigid material while the space between the middle part and the electrode is made of a flexible material. In another embodiment, the middle part of the base 602 is made of a flexible material and the electrodes 104A, 104B are installed on both sides of the flexible part, one on each side. This is shown in FIG. 6 wherein a disposable heart rate indicator 600 of FIG. 6 comprises a part 620 of the base 602, the part 620 having a middle part made of a flexible material. This part 620 is indicated in left-inclined linear markings. The part 620 is capable of yielding at least in a direction indicated by arrow 622. Owing to this flexibility, the distance between the electrodes 104A, 104B may vary. This is advantageous since during respiration the circumference of a person's chest changes. If the base 602 were made of an inflexible material, the electrodes 104A, 104B would not necessarily stay at correct positions on the person's skin for detecting a heart beat, which could make heart rate detection unreliable. When the base 602 yields at least partially (now at the point 602), the electrodes 104A, 104B can stay attached to the skin at the same positions even if the circumference of the chest, and thus the distance between measurement points, change during respiration. This enables a more reliable heart rate indication to be achieved.

In an embodiment, in addition to heart rate indication, the processor is configured to indicate, on the basis of the movement of the chest, whether or not a person is breathing. This may take place by a sensor which measures whether or not the distance between the electrodes 104A, 104B changes. This may be measured e.g. by checking whether or not the base 602 stretches out regularly in accordance with respiration. In an embodiment, the disposable heart rate indicator comprises stretch indicators 626, such as a stretch gauge or a piezoelectric crystal, configured to indicate whether or not the distance between the electrodes changes. Such a separate stretch gauge sensor or a piezoelectric crystal may be installed in the base 602 and configured to be operatively coupled to the processor 106. The processor 106 may indicate the detected respiration to the medical staff by using the light signal emitting head available for this particular purpose, e.g. by means of a light flashing in accordance with the pace of respiration. The signalling light according to this indication may also have a different color than the signalling light indicating a heart rate.

In an embodiment, in addition to heart rate indication, the processor is configured to detect blood oxygen saturation. The oxygen saturation indicates the amount of oxygen bound to red blood cells in relation to the maximum amount of oxygen bound to the red blood cells. In order for the disposable heart rate indicator to be able to establish the oxygen saturation, the heart rate indicator may comprise a light source and a measurement sensor. The light source may be configured to emit light of a certain wavelength towards blood vessels, and the measurement sensor may be configured to measure the amount of light reflected back. This is called near infrared spectroscopy. A detected oxygen saturation value may be indicated by a light signal emitting head which is provided for this particular purpose and which may be e.g. configured to emit light of a certain color when the oxygen saturation is within a range of 90% to 100%, light of another color when the oxygen saturation is less than 90%. The signal light may be lit continuously, for instance. In such a case, the medical staff immediately knows which patient suffers from a low amount of oxygen in blood.

In an embodiment, heart rate indication takes place by a visual light signal, as described above in connection with the different embodiments. The vital functions being monitored may be indicated by a light signal, voice signal, or both. Thus, although in connection with monitoring different vital functions, light signal emitting heads are shown for different vital functions being monitored, instead of or in addition to these light signal emitting heads, voice signal emitting means 624, such as a loudspeaker, could be provided for at least one vital function. The voice signal emitting means 624 may be configured to indicate a heart rate, respiration frequency, oxygen saturation calculation or another vital function to be monitored. In addition to or instead of the above, the voice signal emitting means 624 may be configured to indicate at least one of the following: the electrodes 104A, 104B detect no heart beat, the power source 114 is running low, and the heart rate indicator is ready for operation in connection with being put to use. This is advantageous in that if e.g. in clear weather it is difficult to see a light signal, a voice signal, instead of or in addition to a light signal, may indicate a certain vital function and/or whether or not the heart rate indicator is operational.

In an embodiment, when the heart rate area has been divided into at least two sub-areas, the voice signal emitting means 624 are configured to indicate with a voice signal when sub-areas change. For example, when the heart rate increases to more than 105 beats per minute, the voice signal emitting means 624, such as a loudspeaker, indicates this by a voice signal. The voice signal may be a beep or it may be a given word or group of words, such as "Patient needs attention".

Although in FIGS. 1, 2A, 3A, 4, and 6 the power source 114, the stretch indication means 626, and the voice signal emitting means 624 are shown in the processor 106/606, this is only to indicate that these means are operatively coupled to the processor 106/606 rather than being part thereof.

In an embodiment, the light signal emitting head 108 is wirelessly coupled to the at least two electrodes 108 and to the processor 106. In this case the power necessary for the light signal emitting head 108 and a second processor may in this case be placed in connection with the light signal emitting head 108. The second processor may receive the wireless transmission of information related to the detected heart rate. Thereafter, the second processor may cause the light signal emitting head 108 to operate according any of the embodiments. As the connection between the light signal emitting head 108 and the heart beat detection area 504 is wireless, the conductor means 110 may comprise a wireless radio frequency magnetic interface, such as a Bluetooth® standard. The wireless transmission may utilize electric and/or magnetic fields. The processor 106 and the second processor may comprise required functionalities to perform the wireless transmission and reception, such as transceivers, for example. The conductor means 110 may thus be configured to wirelessly extend from a heart beat detection area 504.

In an embodiment, the processor 106 may wirelessly or via a wire transmit an alarm signal to a predefined central unit. The central unit may be central surveillance unit, for example. The central unit may be monitored by emergency personnel and once the central unit indicates that a certain processor 106 is indicating the alarm signal, the emergency personnel may efficiently be mobilized to the corresponding person in a need of help. The sent alarm signal may be coded so as to identify the processor 106 who transmitted the signal. The processor 106 may decide to send such alarm signal when the heart rate is not within a predetermined window, i.e. exceeds a predetermined high threshold or drops below a predetermined low threshold. Other criteria may be used in addition to or instead of the heart rate, such as the blood oxygen saturation threshold level being crossed.

In an embodiment, the disposable heart rate indicator may comprise a radio frequency identification (RFID) unit, such as a RFID tag or a RFID reader. The RFID tag may be used to identify the person whose vital functions are being or have been monitored by the disposable heart rate indicator. In other words, the RFID may be used to identify the person coupled to the disposable heart rate indicator. The RFIS may be integrated to the disposable hear rate indicator. For example, there may be a need to quickly and reliably identify a person in a hospital or any other facility where the person is getting further medical care.

In an embodiment, the disposable heart rate indicator may be coupled wirelessly or via a wire to an external electrocardiogram (EKG) monitor. The EKG monitor may be used to show with more details, than the light signal emitting head 108, the function of the person's heart. In an embodiment, analog-to-digital (A/D) conversion for the data transmitted to the EKG monitor may be performed at the disposable heart rate indicator, and more particularly at an AD converter comprised in the disposable heart rate indicator, such as in the processor 106 of the disposable heart rate indicator. Then the external EKG monitor may be simple in structure as it only needs to convert the received digital information into visual form.

In an embodiment, the detection of the heart rate may be performed by detecting a QRS complex from the heart beat. The QRS complex may reflect the rapid depolarization of the right and left ventricles of the heart. The QRS complex may much larger amplitude than the P-wave. Therefore, the abnormalities may be spotted easier than by monitoring the P-wave, for example.

In an embodiment, the brightness of the light emitted by the light signal emitting head 108 varies at least partly on the basis of ambient light. In order to enable this, the light signal emitting head 108 may be coupled to an ambient light sensor. This makes it easier to monitor the light signal emitting head 108 even during day time and on bright weathers. On the other hand this may save the battery (i.e. the power source 114) of the disposable heart rate indicator because the light being emitted when it is dark, such as during night time or during cloudy weather, need not be as bright as during the bright weathers.

In an embodiment, the disposable heart rate indicator is coupled wirelessly or via a wire to a unit performing a triage process, which is a process for determining the priority of patients' treatments based on the severity of their condition. The condition of each patient is determined based on at least the heart rate information obtained from the heart rate indicator via the coupling. This is advantageous so that the medical health care personnel immediately may spot which patients need urgent medical attention by looking at the triage unit.

The disposable heart rate indicator according to the different embodiments provides several advantages. First, being simple in structure, it is inexpensive to manufacture. Second, it is lightweight and small, and thus easy to carry around. It has a long shelf life since the power source does not consume power during storage and, being foldable, the heart rate indicator stays clean. It is easy to use and it gives reliable results.

It is extremely easy and quick to place on a patient. The power source 114 is placed close to a person's skin and thus close to the person's body temperature, which extends the life of the power source. The heart rate indicator may be connected to existing ECG equipment. For this purpose, the heart rate indicator may be provided with an appropriate connector which transmits heart beat data to an external ECG device.

It is apparent to one skilled in the art that as technology advances, the basic idea of the invention may be implemented in many different ways. The invention and its embodiments are thus not restricted to the examples described above but may vary within the scope of the claims.

The invention claimed is:

1. A disposable heart rate indicator for indicating a heart rate of an immobile person, comprising:
    a power source for generating power to the heart rate indicator;
    at least two electrodes for detecting a person's heart beat, the electrodes being attachable to the person's skin for duration of use;
    a processor and a light signal emitting head, the processor being operatively coupled to the at least two electrodes and being configured to receive a signal on each heart beat detected by the electrodes and visually indicate a detected heart rate via optical light emitted by the light signal emitting head;
    a base which is at least partly made from a flexible material and wherein the power source, the at least two electrodes and the processor are fixedly installed; and
    a conductor coupled between the light signal emitting head and the processor, the conductor being configured to extend from a heart beat detection area formed by the electrodes and the processor, the conductor being an electrical conductor or an optical conductor;
    wherein the heart rate indicator is configured to be placed on the person's chest underneath clothes, and the conductor is configured to extend from under the person's clothes so as to bring the light signal emitting head outside of the clothing, thus making it visible during use,
    wherein the conductor is extendible in a lengthwise direction and is extendible outside of a surface of the base, thereby allowing the light emitting signal head to be disposed a distance away from the base, and
    wherein the heart rate indicator further comprises a detachment part that is coupled to the conductor, wherein the conductor is configured to extend lengthwise from the base by pulling the detachment part away from the base so that the conductor and light signal emitting head extend from the base and are visible during use.

2. A heart rate indicator as claimed in claim 1, wherein the processor, via the light signal emitting head, is configured to indicate at least one of the following: the electrodes detect no heart beat, the power source is running low, and the heart rate indicator is ready for operation in connection with being put to use.

3. A heart rate indicator as claimed in claim 1, wherein the light signal emitting head is configured to flash in accordance with the pace of the detected heart beats.

4. A heart rate indicator as claimed in claim 1, further comprising:
    a fastener that fastens the light signal emitting head to the person.

5. A heart rate indicator as claimed in claim 1, wherein the processor is configured to:
    divide heart rate area of the person into at least two sub-areas; and produce, via the light signal emitting head, optical light of a predetermined color, wherein the color of the emitted optical light is determined according to the sub-area in which the person's heart rate is at the particular moment.

6. A heart rate indicator as claimed in claim 1, further comprising:
a stretch indicator configured to indicate whether or not a distance between the electrodes changes.

7. A heart rate indicator as claimed in claim 1,
wherein the electrodes are installed in the base such that the distance between the electrodes may change owing to the flexibility of the base.

8. A heart rate indicator as claimed in claim 7, wherein:
the heart rate indicator may be folded up for storage such that sections of the heart rate indicator which in use are placed against the person's skin constitute no part of an outer surface of the folded heart rate indicator.

9. A heart rate indicator as claimed in claim 8, wherein the conductor is, for the duration of storage, arranged inside the folded heart rate indicator and, in use, arranged to extend from the base such that the light signal emitting head is visible during use.

10. A heart rate indicator as claimed in claim 1, wherein the processor is configured to detect blood oxygen saturation in addition to heart rate indication, wherein the heart rate indicator comprises a light source and a measurement sensor, and the light source is configured to emit light of a certain wavelength towards blood vessels and the measurement sensor is configured to measure the amount of light reflected back.

11. A heart rate indicator as claimed in claim 1, further comprising:
a radio frequency identification unit for identifying the person coupled to the heart rate indicator.

12. A heart rate indicator as claimed in claim 1, wherein the heart rate indicator is coupled to an external electrocardiogram monitor, wherein an analog-to-digital conversion for the data transmitted to the external electrocardiogram monitor is performed at the heart rate indicator.

13. A heart rate indicator as claimed in claim 1, wherein the brightness of the light emitted by the light signal emitting head is configured to vary at least partly on the basis of ambient light.

14. A heart rate indicator as claimed in claim 1, further comprising a unit for performing a triage process, wherein the disposable heart rate indicator is coupled to the unit for performing the triage process, wherein the triage process determines the priority of patients' treatment based on the severity of their condition, wherein the condition is determined based on at least the heart rate information obtained from the heart rate indicator via the coupling between the disposable heart rate indicator and the unit for performing the triage process.

15. A heart rate indicator as claimed in claim 1, further comprising a base, wherein the at least two electrodes and the processor are fixedly installed to the base, and the conductor is configured to extend from the base so as to cause the light signal emitting head to be visible during use.

16. A heart rate indicator as claimed in claim 1, wherein the light signal emitting head comprises a light emitting diode (LED).

17. A heart rate indicator as claimed in claim 1, wherein the light signal emitting head comprises at least one of a glue surface, a sticky tape, and a fastening clip for allowing the light signal emitting head to be fastened to a visible place in the person's skin or clothes.

18. A heart rate indicator as claimed in claim 1, wherein the conductor and the light signal emitting head are initially fixed on the base.

19. A heart rate indicator as claimed in claim 1, wherein the detachment part is located off the surface of the base.

* * * * *